(12) United States Patent
Rubinfeld

(10) Patent No.: US 12,109,415 B1
(45) Date of Patent: Oct. 8, 2024

(54) SYSTEM FOR TREATING MEIBOMIAN GLAND DYSFUNCTION

(71) Applicant: Eric Rubinfeld, Yonkers, NY (US)

(72) Inventor: Eric Rubinfeld, Yonkers, NY (US)

(*) Notice: Subject to any disclaimer, the term of this patent is extended or adjusted under 35 U.S.C. 154(b) by 1 day.

(21) Appl. No.: 18/523,381

(22) Filed: Nov. 29, 2023

(51) Int. Cl.
| | | |
|---|---|---|
| *A61N 1/36* | (2006.01) | |
| *A61F 7/02* | (2006.01) | |
| *A61M 21/00* | (2006.01) | |
| *A61N 1/02* | (2006.01) | |
| *A61N 1/04* | (2006.01) | |
| *A61F 7/00* | (2006.01) | |

(52) U.S. Cl.
CPC ............ *A61N 1/36046* (2013.01); *A61F 7/02* (2013.01); *A61M 21/00* (2013.01); *A61N 1/025* (2013.01); *A61N 1/0492* (2013.01); *A61N 1/36034* (2017.08); *A61F 2007/0004* (2013.01); *A61F 2007/0093* (2013.01); *A61M 2021/0072* (2013.01); *A61M 2205/054* (2013.01); *A61M 2205/50* (2013.01); *A61M 2210/0612* (2013.01)

(58) Field of Classification Search
CPC .................. A61N 1/36046; A61N 1/36034
USPC .................................................... 607/3
See application file for complete search history.

(56) References Cited

U.S. PATENT DOCUMENTS

2018/0161579 A1* 6/2018 Franke ................ A61B 5/1127

* cited by examiner

*Primary Examiner* — Nadia A Mahmood
(74) *Attorney, Agent, or Firm* — RC Trademark Company

(57) ABSTRACT

According to some embodiments, a system and method for treating meibomian gland dysfunction is disclosed. The system comprises one or more electrode pads configured for placement on a patient's face on either a lower eyelid, an upper eyelid or both the lower and upper eyelids, a processor and a non-transitory, computer-readable medium. The computer-readable medium stores program code. The program code is executable by a processor to cause the processor to transmit an instruction to the controller to initiate a biofeedback indicator wherein the biofeedback does not cause muscle contraction.

18 Claims, 4 Drawing Sheets

400

```
┌─────────────────────────────────────────────────────────────┐
│  Transmit an instruction to initiate a biofeedback indicator, │
│  wherein the biofeedback does not cause muscle contraction    │
│                                                          402  │
└─────────────────────────────────────────────────────────────┘
                              │
                              ▼
┌─────────────────────────────────────────────────────────────┐
│  Transmit an instruction to one or more electrode pads to provide heat │
│                                                          404  │
└─────────────────────────────────────────────────────────────┘
```

FIG. 4

SYSTEM FOR TREATING MEIBOMIAN GLAND DYSFUNCTION

BACKGROUND

Meibomian gland dysfunction ("MGD") refers to disorders associated with functional abnormalities of the meibomian glands. MGD can lead to altered tear film composition, ocular surface disease, ocular and eyelid discomfort, and evaporative dry eyes. Therefore, a system to treat MGD is desirable.

SUMMARY

Some embodiments described herein relate to a system and method for treating meibomian gland dysfunction is disclosed. The system comprises one or more electrode pads configured for placement on a patient's face on either a lower eyelid, an upper eyelid or both the lower and upper eyelids, a processor and a non-transitory, computer-readable medium. The computer-readable medium stores program code. The program code is executable by a processor to cause the processor to transmit an instruction to the controller to initiate a biofeedback indicator wherein the biofeedback does not cause muscle contraction.

BRIEF DESCRIPTION OF THE DRAWING

FIG. 4 is a method in accordance with some embodiments.

DETAILED DESCRIPTION

In the following detailed description, numerous specific details are set forth in order to provide a thorough understanding of the embodiments. However, it will be understood by those of ordinary skill in the art that the embodiments may be practiced without these specific details. In other instances, well-known methods, procedures, components and circuits have not been described in detail so as not to obscure the embodiments.

Figure 1:
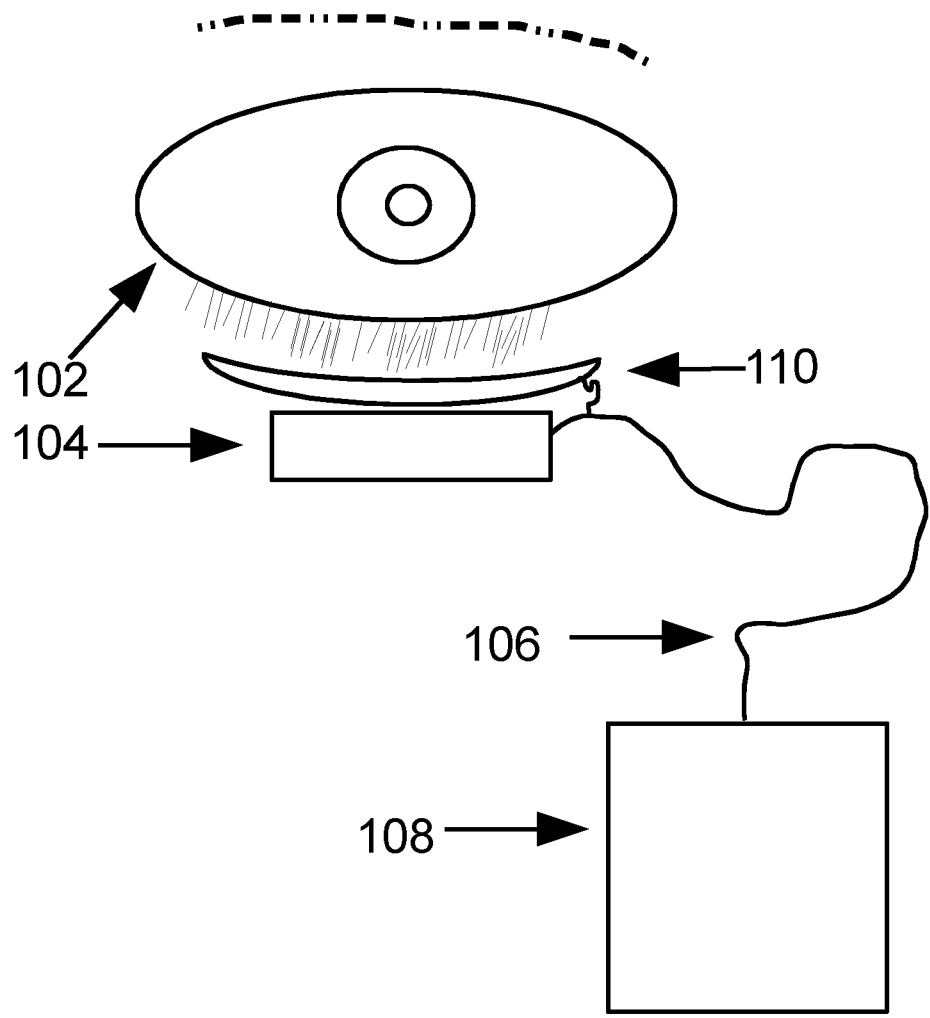
FIG. 1 illustrates a system in accordance with some embodiments.

Now referring to FIG. 1, a system 100 to treat MGD associated with a patient's eye 102 is illustrated. The system comprises one or more electrodes 104 and a controller 108. The electrodes 104 may be in communication with the controller 108 via a wire 106. In some embodiments, a lower, upper or both lower and upper lid strip 110 may also be used. In some embodiments, the one or more electrodes 104 may be in communication with the controller 108 via a wireless communication system (not shown in FIG. 1). The one or more electrodes 104 may be configured for placement on a patient's face near the lower lid, upper lid or near both the upper and lower lip using an upper/lower lid strip as illustrated in FIG. 1. The one or more electrodes 104 may be affixed to the patient's face via a glue or a sticky surface located on one side of the one or more electrodes 104. The one or more electrodes 104 may receive signals from the controller 108 including power and/or control signals. The received signals may instruct the one or more electrodes 104 to provide heat and/or initiate biofeedback where the biofeedback does not cause muscle contraction. The biofeedback may be used as a reminder for the patient to blink. Thus, whenever a patient senses the biofeedback, the patient is reminded to blink. Blinking, at a specific time, in conjunction with heat, may help treat MGD. The blinking action effectively milks the meibomian glands, causing the meibum melting from the heat to be expressed onto the cornea and conjunctiva of the eye. While the biofeedback is the reminder for the patient to blink, the heat is for melting impacted meibomian oil located in an obstructed meibomian gland of the upper and lower eyelids.

Figure 2:
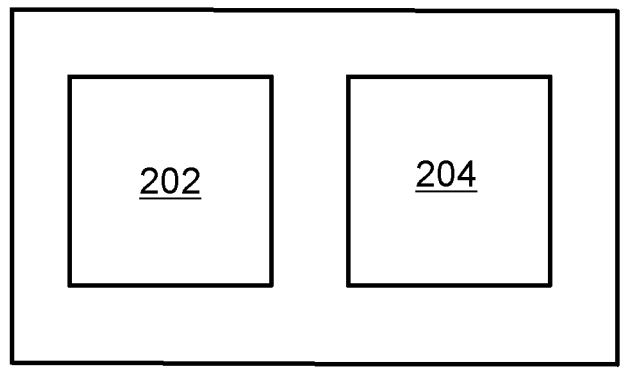
FIG. 2 illustrates an electrode pad in accordance with some embodiments.

Now referring to FIG. 2, an embodiment of an electrode pad 200 is illustrated. The electrode pad 200 may comprise a gel pad that is configured to emit EMS (electro muscle stimulation) and heat.

In some embodiments, the electrode 200 may comprise a first portion 202 the applies heat to the patient and a second portion 204 for providing the biofeedback that the patient can feel/hear/sense. In some embodiments, the biofeedback may comprise a voltage level that is low enough such that it does not cause muscle contractions. However, the controller 108 can set the level of the voltage so that it can be raised if the patient does not feel the pulse and the voltage can be lowered if the pulse is causing muscle contractions. The pulse may comprise EMS (electro muscle stimulation) to the orbicularis muscle of the lower eye lid for alerting the patient to blink. The pulse may be felt by placing the electrode 204 on a patient's face near the lower eyelid such as a location above the orbicularis oculi of the lower eyelid. The pulses may be provided every from 4-12 seconds. However, the timing of the pulses may be adjusted as needed by the treating physician. In some embodiments, the second portion 204 may function by vibration. In this embodiment, the second portion 204 may comprise a speaker that provides a "an audible tone" to the patient's face. In this embodiment, a vibration and/or sound may be initiated every 4-12 seconds as a reminder for the patient to blink. In yet another embodiment, the controller 108, as described with respect to FIG. 1, may comprise a speaker that provides an audible tone that the patient may hear. In this embodiment, a tone may be played from the controller 108 every 4-12 seconds as a reminder for the patient to blink.

The first portion 202 may apply heat based on receiving a voltage from the controller 108 where the voltage is sufficient enough to cause a heating element to produce heat. In this regard, a level of heat is may be adjusted based on the patient by controlling the voltage sent to the first portion 202. For example, if a higher heat is needed to melt impacted meibomian oil, an increased voltage may be sent to the first portion. In some cases, when the heat is too great for a patient, a lower voltage may reduce the heat generated by the first portion 202.

Based on commands from the controller 108, the first portion 202 may gradually increase the temperature over a first two to three minutes until a temperature of between 41-45° C. is reached. In some embodiments, this temperature may be reached within thirty (30) seconds. This temperature may be increased or decreased needed as determined by a treating physician. The electrode pad 200 may be square shaped or may be an arcuate shape to follow a boarder of one or more eyelids.

In some embodiments, besides the electrode pad 200, a lower lid strip 110 that includes an arcuate shape to follow a border of the eyelid is also used. The lower lip strip 110 further includes an arcuate periphery which is shaped to extend and follow a free margin of a lower eyelid.

Figure 3:
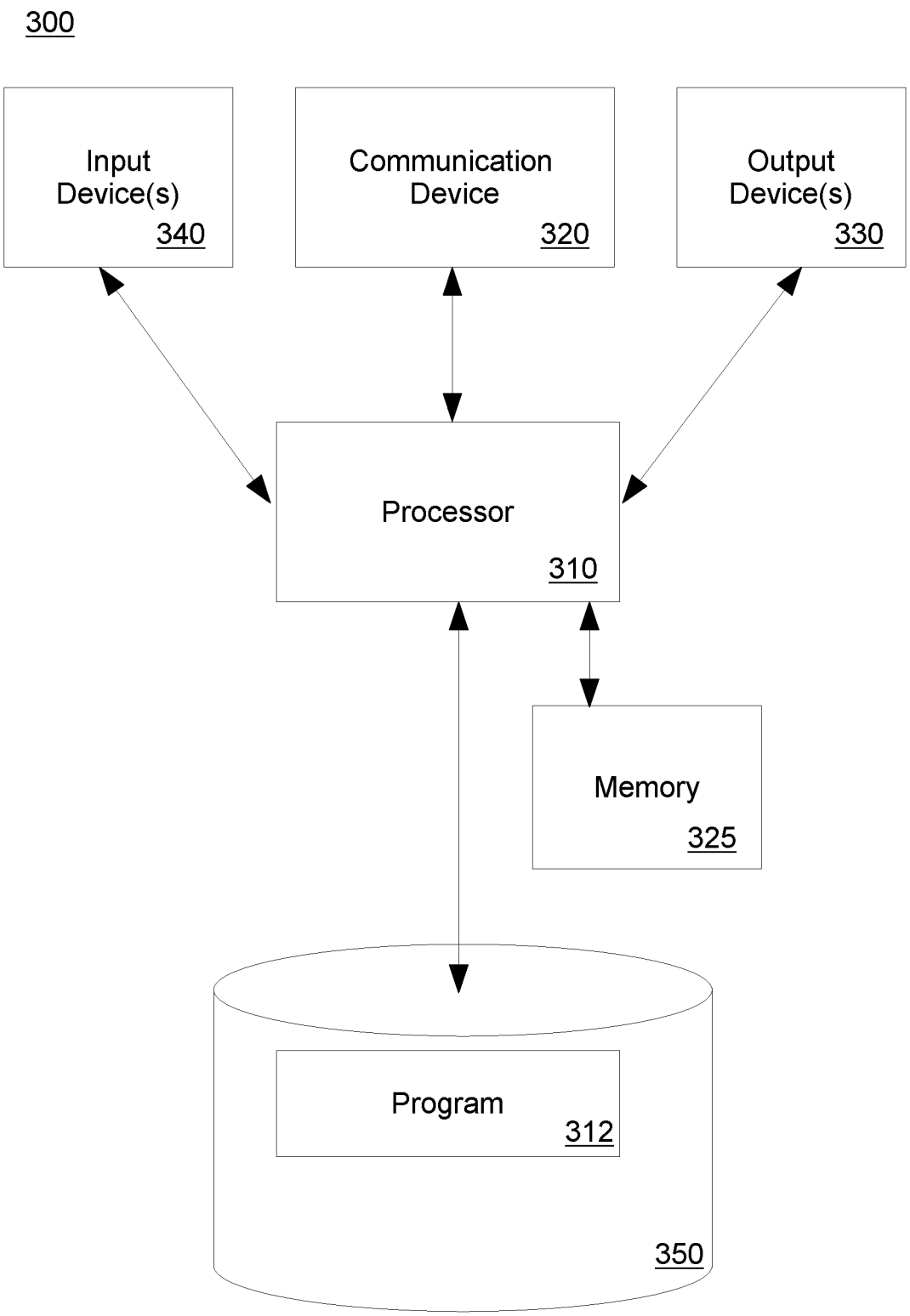
FIG. 3 illustrates a controller in accordance with some embodiments.

Referring now to FIG. 3, and embodiment of a controller 300 is illustrated. The controller 300 may be battery powered. The controller 300 may provide a technical and commercial advantage by being able to facilitate the application of heat to a patient's meibomian glands while providing a biofeedback mechanism to remind the patient to blink. The blinking action effectively milks the meibomian glands, causing the meibum melting from the heat to be expressed onto the cornea and conjunctiva of the eye.

The controller 300 may comprise a processor 310 ("processor"), such as one or more commercially available Central Processing Units (CPUs) in the form of one-chip microprocessors, coupled to a communication device 320 configured to communicate via a communication network (not shown in FIG. 3). The communication device 320 may be used to communicate, for example, with one or more electrodes affixed to a patient's face. The controller300 further includes an input device 340 (e.g., a mouse and/or keyboard to control levels of heat and biofeedback) and an output device 330 (e.g., to output and levels of heat and biofeedback).

The processor 310 also communicates with a memory 325 and storage device 350 that stores data 313. The storage device 350 may comprise any appropriate information storage device, including combinations of magnetic storage devices (e.g., a hard disk drive), optical storage devices, mobile telephones, and/or semiconductor memory devices. The storage device 350 may store a program 312 for controlling the processor 310. The processor 310 performs instructions of the programs 412 and thereby operates in accordance with any of the embodiments described herein. For example, the processor 310 may receive levels of heat and timing of biofeedback via the instructions of the programs 312.

The program 312 may be stored in a compiled, compressed, uncompiled and/or encrypted format or a combination. The programs 412 may furthermore include other program elements, such as an operating system, a database management system, and/or device drivers used by the processor 310 to interface with peripheral devices.

Referring now to FIG. 4, a method 400 is illustrated. At 402, an instruction is transmitted to initiate a biofeedback indicator wherein the biofeedback does not cause muscle contraction. At 404, an instruction is transmitted to the one or more electrode pads to provide heat.

As will be appreciated by one skilled in the art, the present embodiments may be embodied as a system, method, or computer program product. Accordingly, the embodiments described herein may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the embodiments described herein may take the form of a computer program product embodied in one or more computer readable medium(s) having computer readable program code embodied thereon.

This written description uses examples to disclose multiple embodiments, including the preferred embodiments, and to enable any person skilled in the art to practice the invention, including making and using any devices or systems and performing any incorporated methods. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

What is claimed:

1. A system for treating meibomian gland dysfunction, the system comprising:
    one or more electrode pads configured for placement on a patient's face near a lower eyelid, an upper eyelid or both an upper eyelid and a lower eyelid;
    a processor; and
    a non-transitory, computer-readable medium storing program code, the program code executable by a processor to cause the processor to:
    transmit an instruction to initiate a biofeedback indicator, wherein the biofeedback does not cause muscle contraction, wherein the instruction to initiate the biofeedback indicator is transmitted to a speaker disposed on the one or more electrode pads or the controller, wherein the biofeedback indicator is a tone and wherein the program code further causes the processor to: transmit an instruction to the one or more electrode pads to provide heat, and wherein the biofeedback and the heat are for melting impacted meibomian oil located in an obstructed meibomian gland of the upper and lower eyelids by providing heat and a biofeedback function to remind the patient to blink.

2. The system of claim 1, wherein the biofeedback is a sound, vibration or pulse.

3. The system of claim 1, wherein a level of the biofeedback may be adjusted based on a patient.

4. The system of claim 1, wherein the heat may be adjusted based on the patient.

5. The system of claim 1, wherein the system automatically and gradually increases a temperature over a first two to three minutes until a temperature of between 41-45° C. is reached.

6. The system of claim 1, wherein the system automatically and gradually increases a temperature over thirty seconds until a temperature of between 41-45° C. is reached.

7. The system of claim 6, wherein the biofeedback comprises EMS (electro muscle stimulation) to the orbicularis muscle of the lower lids for alerting the patient to blink.

8. The system of claim 1, wherein the biofeedback is provided every from 4-12 seconds.

9. The system of claim 1, wherein the one or more electrode pads are gel pads that is configured to emit EMS and heat.

10. The system of claim 1, further comprising a lower lid strip including an arcuate shape to follow a border of one or more eyelids.

11. The system of claim 10, wherein the lower lid strip further includes an arcuate periphery which is shaped to extend and follow a free margin of the lower eyelid, upper eyelid or a combination of the lower and upper eyelids.

12. The system of claim 1, wherein placement on a patient's face near the lower eyelid comprises a location above the orbicularis oculi of the lower eyelid.

13. A system for treating meibomian gland dysfunction, the system comprising:
    one or more electrode pads configured for placement on a patient's face near a lower eyelid, an upper eyelid or both an upper eyelid and a lower eyelid;
    a processor;
    a non-transitory, computer-readable medium storing program code, the program code executable by a processor to cause the processor to:

transmit an instruction to (i) initiate biofeedback wherein the biofeedback does not cause muscle contraction and (ii) provide heat via the one or more electrode pads, wherein the system automatically and gradually increases the temperature over the first two to three minutes until a temperature of between 41-45° C. is reached and the biofeedback is provided every from 4-12 seconds.

14. The system of claim 13, wherein the instruction to initiate the biofeedback indicator is transmitted to a speaker disposed on the one or more electrode pads or the controller, wherein the biofeedback indicator is a tone.

15. The system of claim 13, wherein a biofeedback may be adjusted based on a patient.

16. The system of claim 15, wherein the heat may be adjusted based on the patient.

17. The system of claim 13, wherein the biofeedback and the heat are for melting impacted meibomian oil located in an obstructed meibomian gland of the upper and lower eyelids by providing heat and a biofeedback function to remind the patient to blink.

18. A system for treating meibomian gland dysfunction, the system comprising:
one or more electrode pads configured for placement on a patient's face near a lower eyelid, an upper eyelid or both an upper eyelid and a lower eyelid;
a processor; and
a non-transitory, computer-readable medium storing program code, the program code executable by a processor to cause the processor to:
transmit an instruction to initiate a biofeedback indicator, wherein the biofeedback does not cause muscle contraction, wherein the instruction to initiate the biofeedback indicator is transmitted to a speaker disposed on the one or more electrode pads or the controller, wherein the biofeedback indicator is a tone and wherein the program code further causes the processor to:
transmit an instruction to the one or more electrode pads to provide heat, wherein the system automatically and gradually increases a temperature over thirty seconds until a temperature of between 41-45° C. is reached.

* * * * *